United States Patent
Zar et al.

(10) Patent No.: US 9,875,578 B2
(45) Date of Patent: Jan. 23, 2018

(54) VOXELIZATION OF A MESH

(71) Applicant: Biosense Webster (Israel) Ltd., Yokneam (IL)

(72) Inventors: Lior Zar, Poria Illit (IL); Natan Sharon Katz, Atlit (IL); Benjamin Cohen, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 85 days.

(21) Appl. No.: 14/881,192

(22) Filed: Oct. 13, 2015

(65) Prior Publication Data

US 2017/0103570 A1 Apr. 13, 2017

(51) Int. Cl.
| | |
|---|---|
| G06T 17/20 | (2006.01) |
| G06T 15/00 | (2011.01) |
| G06T 15/08 | (2011.01) |
| A61B 34/10 | (2016.01) |
| A61B 5/06 | (2006.01) |
| G06T 17/00 | (2006.01) |

(52) U.S. Cl.
CPC ............ *G06T 17/205* (2013.01); *A61B 5/062* (2013.01); *A61B 34/10* (2016.02); *G06T 15/005* (2013.01); *G06T 15/08* (2013.01); *G06T 17/00* (2013.01); *G06T 17/20* (2013.01); *A61B 2034/105* (2016.02)

(58) Field of Classification Search
None
See application file for complete search history.

(56) References Cited

U.S. PATENT DOCUMENTS 6,867,774 B1 * 3/2005 Halmshaw ............ G06T 15/08
345/424
8,274,513 B1 9/2012 Ubieto
(Continued)

FOREIGN PATENT DOCUMENTS

| EP | 2 728 552 A2 | 5/2014 |
| EP | 2 902 973 A1 | 8/2015 |

OTHER PUBLICATIONS

European Search Report dated Mar. 8, 2017 from corresponding European Patent Application No. 16193486.4.
(Continued)

*Primary Examiner* — Edward Martello
(74) *Attorney, Agent, or Firm* — Vincent J. Serrao

(57) ABSTRACT

A method for 3D rendering, including receiving a group of 3D triangles defining a mesh of a surface, each 3D triangle in the group having 3D vertices with respective 3D coordinates, and transforming each 3D triangle into a 2D triangle having 2D vertices corresponding respectively to the 3D vertices, each 2D vertex having respective 2D pixel coordinates and a triplet of pixel attributes corresponding to the 3D coordinates of a corresponding 3D vertex. Each 2D triangle is passed to a graphics processor, which treats the triplet of pixel attributes of each 2D vertex as interpolatable values. The graphics processor computes respective triplets of interpolated pixel attributes for pixels within each 2D triangle by interpolation between the pixel attributes of the 2D vertices, and a 3D image of the surface is rendered by converting the interpolated pixel attributes computed by the graphics processor into voxel coordinates in the 3D image.

16 Claims, 4 Drawing Sheets

(56) References Cited

U.S. PATENT DOCUMENTS

2003/0038802 A1* 2/2003 Johnson .................. G06T 17/30
345/420
2004/0006450 A1* 1/2004 Hale ....................... G06T 17/20
702/189

OTHER PUBLICATIONS

Benes, Bedrich et al., "GI-COLLIDE—Collision Detection with Geometry Images", Proceeding of SCCG '05—$21^{st}$ Spring Conference on Computer Graphics, Budmerice, Slovakia, May 12-14, 2005, pp. 95-102.

Carr, Nathan A. et al., "Fast GPU Ray Tracing of Dynamic Meshes using Geometry Images", Graphics Interface 2006, Jun. 7, 2006, pp. 203-209.

Praun, Emil et al., "Spherical Parametrization and Remeshing", ACM Siggraph 2003 Papers, Jul. 1, 2003, pp. 340-349.

* cited by examiner

VOXELIZATION OF A MESH

FIELD OF THE INVENTION

The present invention relates generally to image generation, and specifically to efficient generation of an image from a mesh.

BACKGROUND OF THE INVENTION

In many fields it is important to be able to manipulate images in a timely manner. The manipulation becomes more computer intensive as the resolution, size and numbers of colors in the image increases. In time critical fields, such as during a surgical procedure, the manipulation may be required to be in substantially real-time, leading to further demands on computer resources used to present the image. In some cases, in order to maintain real-time behavior, the quality of the image may be reduced, for example by reducing the resolution of the image or by reducing the number of colors in the image.

SUMMARY OF THE INVENTION

An embodiment of the present invention provides a method for three-dimensional (3D) rendering, including:

receiving a group of 3D triangles defining a triangular mesh of a surface, each 3D triangle in the group having three 3D vertices with respective 3D coordinates;

transforming each 3D triangle into a corresponding two-dimensional (2D) triangle having three 2D vertices corresponding respectively to the 3D vertices, each 2D vertex having respective 2D pixel coordinates and a triplet of pixel attributes corresponding to the 3D coordinates of a corresponding 3D vertex;

passing each 2D triangle to a graphics processor, which treats the triplet of pixel attributes of each 2D vertex as interpolatable values;

in the graphics processor, computing respective triplets of interpolated pixel attributes for pixels within each 2D triangle by interpolation between the pixel attributes of the 2D vertices of the 2D triangle; and rendering a 3D image of the surface by converting the interpolated pixel attributes computed by the graphics processor into voxel coordinates in the 3D image.

The method typically includes, after passing a given 2D triangle to the graphics processor, filling the given 2D triangle with the pixels within the given 2D triangle.

In a disclosed embodiment the interpolated pixel attributes include a weighted interpolation of the triplet of pixel attributes of each 2D vertex. Typically the weighted interpolation includes applying a weight to the triplet of pixel attributes of a given 2D vertex that is inversely proportional to a distance of a given pixel to the given 2D vertex.

In a further disclosed embodiment converting the interpolated pixel attributes into voxel coordinates consists of enclosing the triangular mesh in a rectangular parallelepiped of voxels, and selecting voxels containing or touching the interpolated pixel attributes as voxels of the surface.

In a yet further disclosed embodiment the surface is included in a chamber of a heart.

In an alternative embodiment there is one common 2D triangle for all the 3D triangles.

In a further alternative embodiment each 2D triangle is configured to fill a virtual screen.

There is further provided, according to an embodiment of the present invention, apparatus for three-dimensional (3D) rendering, including:

a processing unit configured to:

receive a group of 3D triangles defining a triangular mesh of a surface, each 3D triangle in the group having three 3D vertices with respective 3D coordinates, and transform each 3D triangle into a corresponding two-dimensional (2D) triangle having three 2D vertices corresponding respectively to the 3D vertices, each 2D vertex having respective 2D pixel coordinates and a triplet of pixel attributes corresponding to the 3D coordinates of a corresponding 3D vertex; and a graphics processor configured to:

receive each 2D triangle and to treat the triplet of pixel attributes of each 2D vertex as interpolatable values, compute respective triplets of interpolated pixel attributes for pixels within each 2D triangle by interpolation between the pixel attributes of the 2D vertices of the 2D triangle, and wherein the processing unit is configured to render a 3D image of the surface by converting the interpolated pixel attributes computed by the graphics processor into voxel coordinates in the 3D image.

The present disclosure will be more fully understood from the following detailed description of the embodiments thereof, taken together with the drawings, in which:

DETAILED DESCRIPTION OF EMBODIMENTS

Overview

Figure 1:
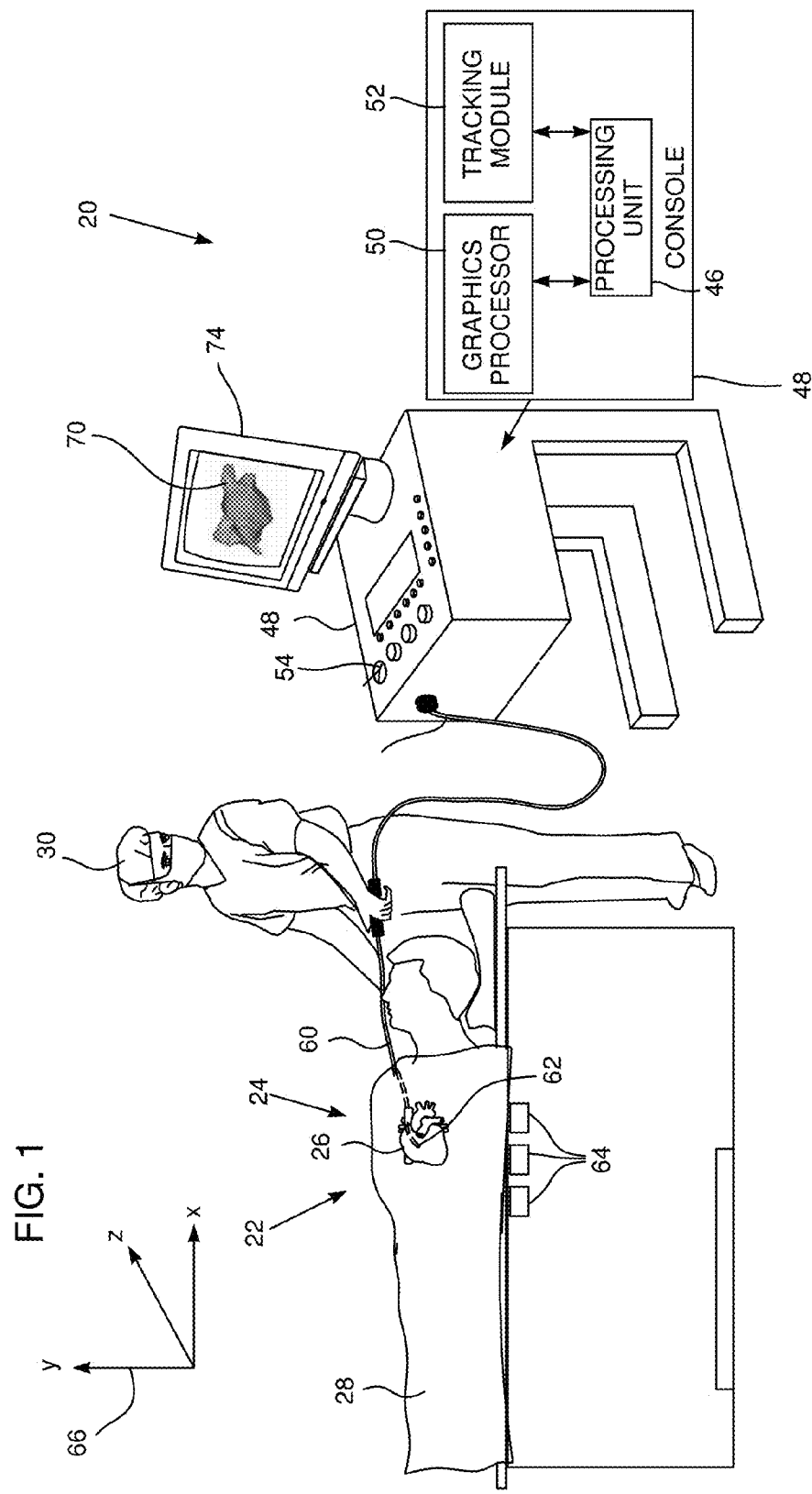
FIG. 1 is a schematic illustration of a voxelization apparatus, according to an embodiment of the present invention.

Manipulation of surface images, such as rotating, translating, magnifying, and/or de-magnifying the images is typically computer intensive. Furthermore, as the resolution of images and number of colors in the images increase, the computing power needed to perform the manipulations in a timely manner also needs to increase. Rather than provide such increased computing power, prior art systems may reduce the resolution of the image, reduce the number of colors, and/or increase the time taken for manipulating the image.

Embodiments of the present invention take a different tack, by providing the increased computing power needed for quick manipulations of images having a high resolution. The increased computer power is provided in the form of a dedicated graphics processor. As is known in the art, a graphics processor has a highly parallel structure, which makes it more effective than general purpose processing units for processing large blocks of data.

In embodiments of the present invention a general purpose processing unit receives a group of three-dimensional (3D) triangles that define a mesh of a surface, each of the triangles having three 3D vertices with respective 3D coordinates. The processing unit transforms each 3D triangle into a corresponding two-dimensional (2D) triangle having three 2D vertices corresponding to the 3D vertices. Typically, although the 3D triangles are different, the 2D triangles may be one common 2D triangle, having one set of 2D vertices. Each 2D vertex has 2D pixel coordinates, and in addition each vertex is assigned a triplet of pixel attributes that are the 3D coordinates of a corresponding 3D vertex.

The processing unit passes each 2D triangle to a dedicated graphics processor which treats the triplet of pixel attributes of each 2D vertex as interpolatable values, i.e., values between which the graphics processor may perform interpolation. In some usages of a graphics processor, the interpolatable values input to the processor are color values. The graphics processor is configured to fill each 2D triangle with pixels within the triangle. Furthermore, by treating the triplet of pixel attributes of each 2D vertex as interpolatable values, the graphics processor computes respective triplets of interpolated pixel attributes for each of the filled pixels. The interpolation is typically a weighted mean of the 2D vertex triplets, the weighting being configured to be inversely proportional to the distance of a given filled pixel from the 2D vertices.

The processing unit may receive the triplets of interpolated pixel attributes from the graphics processor, and use the triplets as 3D points within the corresponding 3D triangle. The processing unit typically initially encloses the mesh in a set of voxels, and after performing the process described above, selects voxels that enclose or touch the 3D points. The processing unit then uses voxel coordinates of the selected voxels to render a 3D image of the surface associated with the mesh on a screen.

By using a dedicated graphics processor which is configured to treat a triplet of pixel attributes as interpolatable values, embodiments of the present invention use the highly parallel nature of the graphics processor to efficiently manipulate high resolution images in real time.

System Description

In the following description, like elements in the drawings are identified by like numerals, and the like elements are differentiated as necessary by appending a letter to the identifying numeral.

FIG. 1 is a schematic illustration of a voxelization apparatus 20, according to an embodiment of the present invention. As is described hereinbelow, apparatus 20 is configured to determine voxels comprised in a three-dimensional (3D) surface 22. By way example, the apparatus is assumed to be used in an invasive medical procedure, and surface 22 upon which the procedure is performed is assumed to comprise the surface of a chamber 24 of a heart 26 of a human patient 28. The procedure is assumed to be performed by a medical professional 30. Also by way of example, the procedure is assumed to comprise ablation of surface 24. However, it will be understood that embodiments of the present invention are not just applicable to this specific procedure on a particular surface, and may include substantially any procedure on any surface.

Apparatus 20 is controlled by a system processing unit (PU) 46, which is located in an operating console 48 of the apparatus. PU 46 is in communication with a graphics processor (GP) 50 and with a tracking module 52, the functions of which are described below. PU 46 is typically also in communication with other modules used for the procedure, such as an ablation module and an irrigation module, but for simplicity such modules are not shown in FIG. 1. Console 48 comprises controls 54 which are used by professional 30 to communicate with the processing unit.

Typically, prior to performing the procedure, surface 22 is mapped, and the mapping is assumed to be performed by professional 30. In order to perform the mapping a probe 60 may be configured to have a location sensor 62 at its distal end, the location sensor being in communication with PU 46 so that signals from the sensor enable the processing unit to determine the location of the sensor. Sensor 62 may use any method for determining its location known in the art. For example, sensor 62 may comprise one or more coils, and PU 46 may use a magnetic tracking method, wherein magnetic transmitters 64 external to patient 28 generate signals in the coils. The processing unit may use a tracking module, such as tracking module 52, to convert the signals to location coordinates in a three-dimensional (3D) frame of reference 66 defined by the magnetic transmitters. In FIG. 1 the 3D frame of reference is illustrated by a set of orthogonal xyz axes. The Carto® system produced by Biosense Webster, of Diamond Bar, Calif., uses such a tracking method.

To perform the mapping the professional may insert probe 60 into a lumen of the patient, so that the distal end of the probe enters chamber 24 of the heart of the patient, and so that sensor 62 contacts surface 22 of the chamber at multiple points. From the mapping PU 46 may generate an image 70 of surface 22, which the processing unit typically presents to professional 30 on a screen 74. During the procedure professional 30 is able to manipulate image 70, for example by rotating, changing the magnification, changing the direction of view, and/or showing only a portion of the image, using controls 54. The production of image 70 is described below.

The software for PU 46, GP 50, and module 52 may be downloaded in electronic form, over a network, for example. Alternatively or additionally, the software may be provided on non-transitory tangible media, such as optical, magnetic, or electronic storage media.

Figure 2:
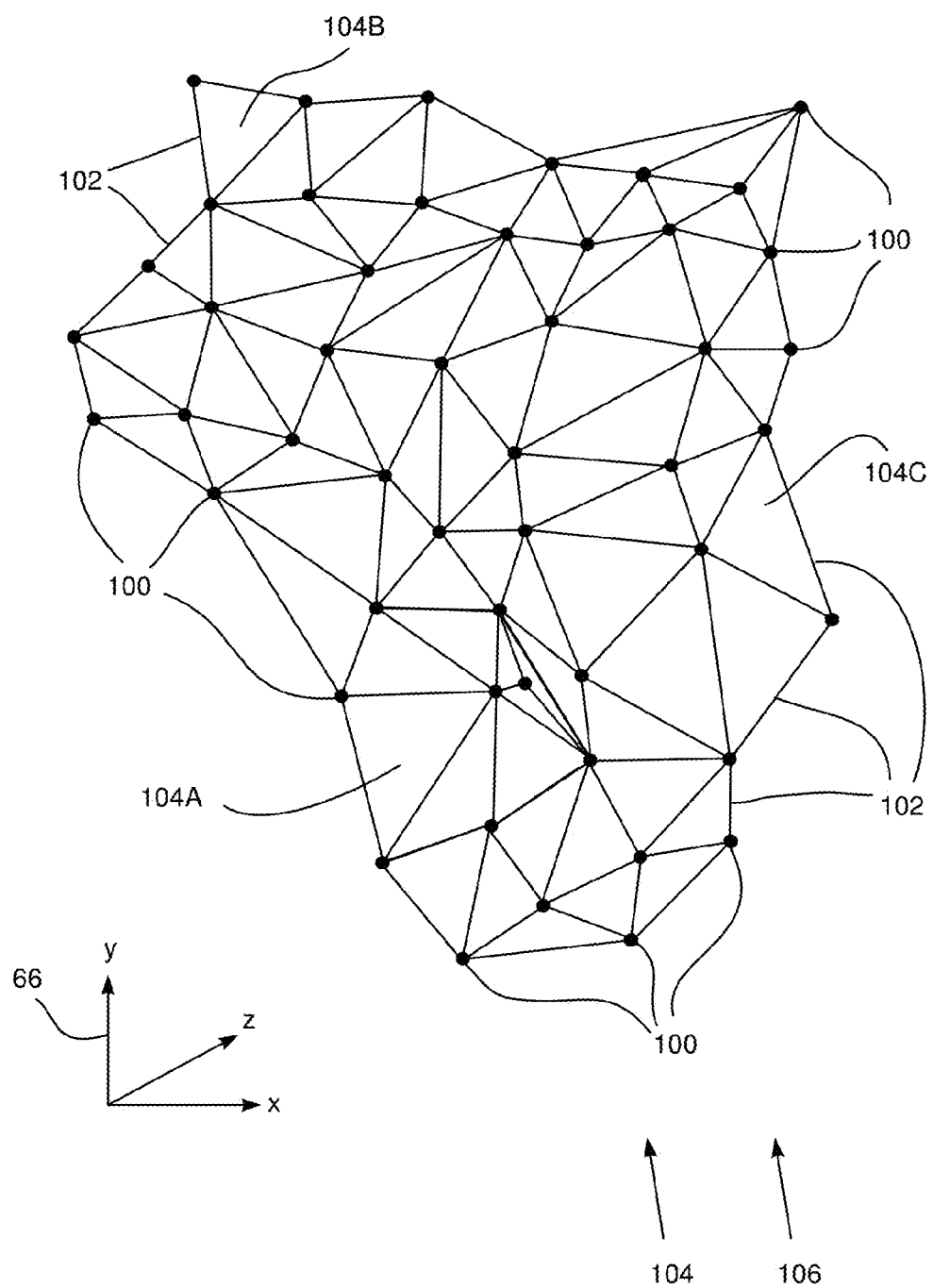
FIG. 2 is a schematic illustration of points that are registered by a sensor as it contacts a surface, according to an embodiment of the present invention.

FIG. 2 is a schematic illustration of points 100 that are registered by sensor 62 as it contacts surface 22, according to an embodiment of the present invention. Typically during the mapping referred to above, PU 46 initially stores 3D coordinates of points 100 as measured in the 3D frame of reference defined by transmitters 64. The processing unit then connects 3D coordinates of points 100, herein also termed 3D vertices 100, by line segments 102, using any method known in the art such as the ball-pivoting algorithm, to produce a set of connected 3D triangles 104A, 104B, 104C, . . . , generically termed triangles 104. 3D triangles 104 form a triangular mesh 106 of the surface. As described below with reference to the flowchart of FIG. 3, PU 46 uses GP 50 to render mesh 106 into image 70.

Figure 3:
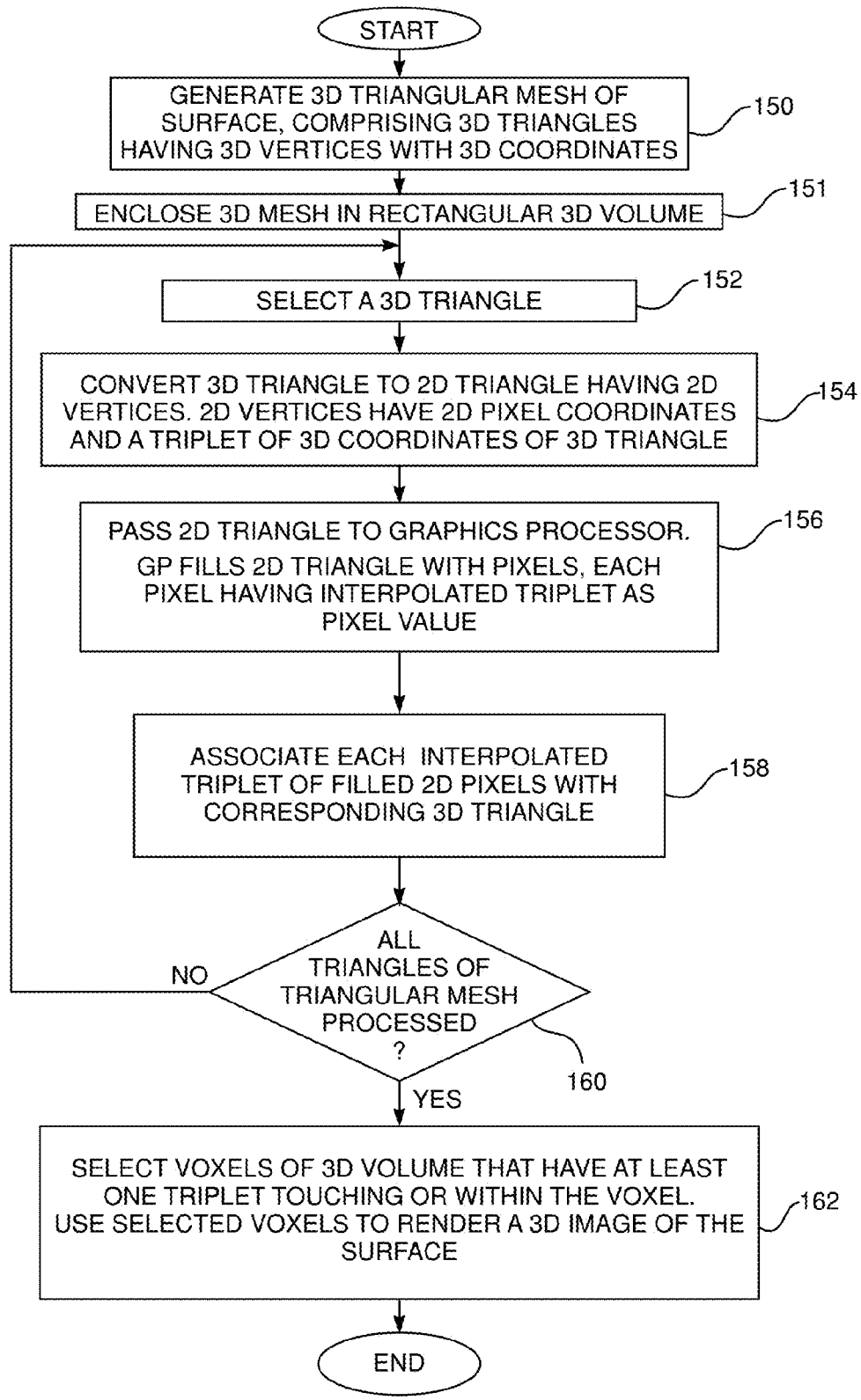
FIG. 3 is a flowchart of steps performed by a processing unit to produce an image, according to an embodiment of the present invention.
Figure 4:
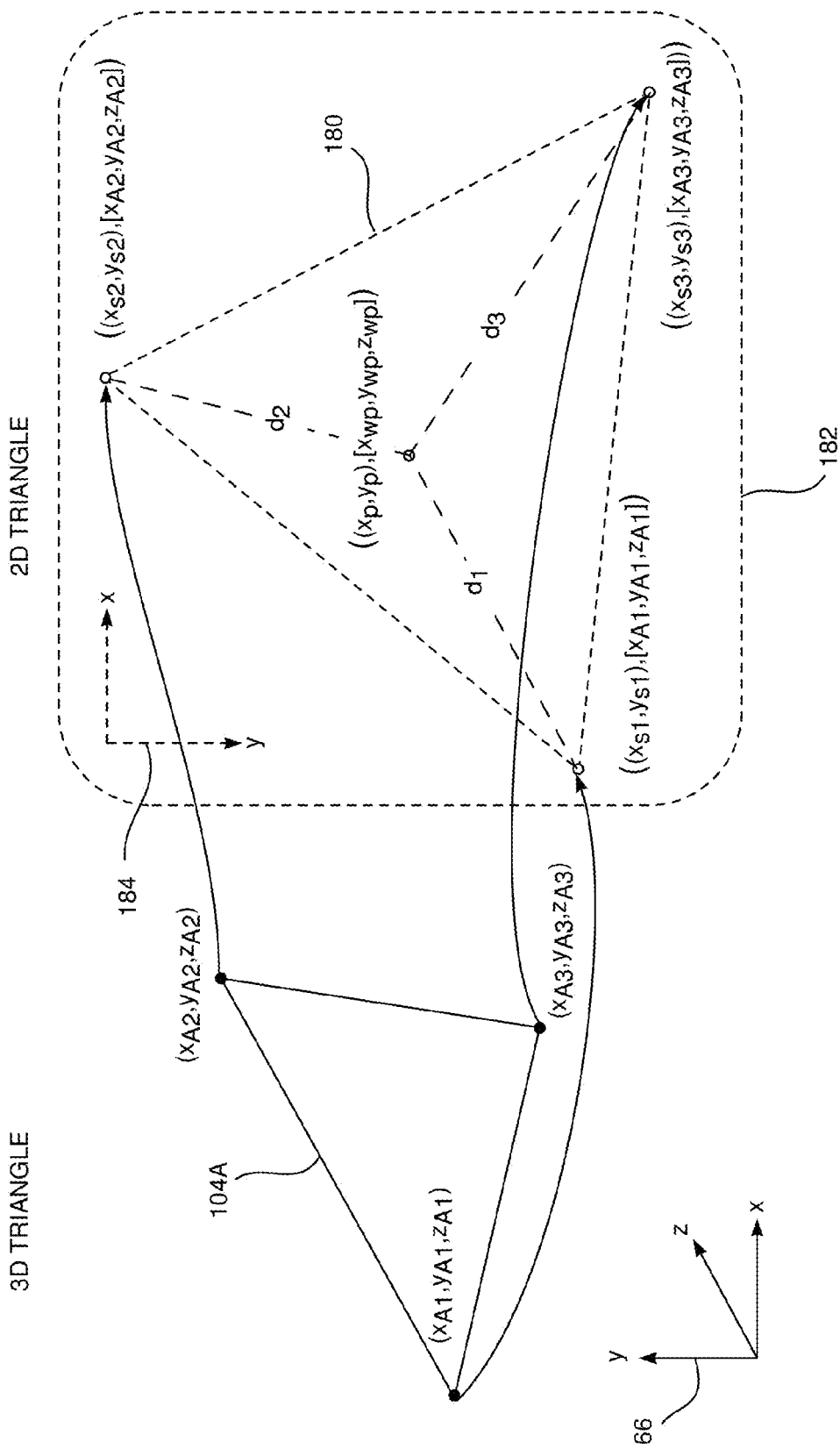
FIG. 4 is a diagram illustrating one of the steps of the flowchart, according to an embodiment of the present invention.

FIG. 3 is a flowchart of steps performed by PU 46 to produce image 70, and FIG. 4 is a diagram illustrating one of the steps of the flowchart, according to an embodiment of the present invention. In an initial step 150, the processing unit generates a 3D triangular mesh, herein assumed to comprise mesh 106, of surface 22, generally as described above with reference to FIGS. 1 and 2. The generation of the mesh comprises determining 3D coordinates, as ordered triplets, of 3D vertices 100 of the mesh, then determining equations of line segments 102 connecting the vertices to form 3D triangles 104, in frame of reference 66.

In an enclosure step 151, the 3D mesh is enclosed in a 3D volume composed of voxels. Typically, although not necessarily, edges of the enclosing volume are selected to be parallel to the xyz axes of frame of reference 66. The number and size of the voxels may be selected by professional 30. The voxels are typically cubic and are typically equal in size. Typical 3D volumes may comprise 128×128×128 or 512×512×512 voxels, but embodiments of the present invention are not limited to these specific values, and other convenient voxel configurations for the 3D volume may be selected by professional 30. In a triangle selection step 152, the processing unit selects a 3D triangle, herein assumed to be triangle 104A, and registers the 3D coordinates of the 3D vertices of the triangle, assumed to be triplets $(x_{A1}, y_{A1}, z_{A1})$, $(x_{A2}, y_{A2}, z_{A2})$, $(x_{A3}, y_{A3}, z_{A3})$.

In a conversion step 154, in preparation for inputting data to GP 50, the selected 3D triangle is converted to a 2D triangle. Each of the 3D coordinates of the 3D vertices of the selected triangle is placed in a one-one correspondence with respective 2D coordinates of two-dimensional (2D) vertices. Each of the 2D vertices has 2D pixel coordinates and a triplet of pixel attributes of the corresponding 3D vertex.

FIG. 4 and Table I below illustrate the correspondence formed in step 154.

TABLE I

| 3D Triangle<br>3D Vertices | 2D Triangle<br>2D Vertices and Pixel Triplet |
|---|---|
| $(x_{A1}, y_{A1}, z_{A1})$ | $((x_{s1}, y_{s1}), [x_{A1}, y_{A1}, z_{A1}])$ |
| $(x_{A2}, y_{A2}, z_{A2})$ | $((x_{s2}, y_{s2}), [x_{A2}, y_{A2}, z_{A2}])$ |
| $(x_{A3}, y_{A3}, z_{A3})$ | $((x_{s3}, y_{s3}), [x_{A3}, y_{A3}, z_{A3}])$ |

FIG. 4 illustrates 3D triangle 104A, with its three 3D vertices, drawn in frame of reference 66. A 2D triangle 180, corresponding to 3D triangle 104A, has been drawn on a 2D screen 182 which has a 2D frame of reference 184. Triangle 180, screen 182, and frame of reference 184 have been drawn in broken lines, to indicate that the correspondence generated in step 154 does not involve any actual placement of points on a screen, and that screen 182 is a virtual screen. Thus, 2D triangle 182 is drawn in broken lines since there is no actual drawing of triangle 182.

As is described further below, step 154 is repeated for different 3D triangles selected in step 152. However, while the 3D triangles may be different, the 2D triangle into which they are converted may be the same, so that in this case there is one common 2D triangle for all the 3D triangles. In some embodiments the 2D vertices of the common 2D triangle are selected so that the 2D triangle fills screen 182. In this case, and assuming that screen 182 in frame of reference 184 has corners (1, 1), (1, -1), (-1, -1), and (-1, 1) Table II applies for the correspondence.

TABLE II

| 3D Triangle<br>3D Vertices | 2D Triangle<br>2D Vertices and Pixel Triplet |
|---|---|
| $(x_{A1}, y_{A1}, z_{A1})$ | $((0.0, 1.0), [x_{A1}, y_{A1}, z_{A1}])$ |
| $(x_{A2}, y_{A2}, z_{A2})$ | $((-1.0, -1.0), [x_{A2}, y_{A2}, z_{A2}])$ |
| $(x_{A3}, y_{A3}, z_{A3})$ | $((1.0, -1.0), [x_{A3}, y_{A3}, z_{A3}])$ |

In a GP input and filling step 156, PU 46 passes the 2D vertices and associated pixel triplets of the 2D triangle to GP 50. GP 50 is configured, on receipt of the three 2D vertices, to fill triangle 182 with 2D pixels, each 2D pixel having respective 2D screen coordinates $(x_p, y_p)$, p=1, 2, 3, . . . .

In addition, the GP is configured to treat the attributes of each pixel triplet associated with the 2D vertices as interpolatable values. As for its treatment of interpolatable values, for each interpolated 2D pixel $(x_p, y_p)$ the GP calculates a value of a pixel triplet $[x_{wp}, y_{wp}, z_{wp}]$ associated with the pixel as the weighted average of the three pixel triplets of the 2D vertices of triangle 182, the weighting being determined according to the closeness of the interpolated pixel to the vertices.

An expression for $[x_{wp}, y_{wp}, z_{wp}]$ is given by equation (1):

$$[x_{wp}, y_{wp}, z_{wp}] \equiv \begin{bmatrix} w_1 x_{A1} + w_2 x_{A2} + w_3 x_{A3}, \\ w_1 y_{A1} + w_2 y_{A2} + w_3 y_{A3}, w_1 z_{A1} + w_2 z_{A2} + w_3 z_{A3} \end{bmatrix} \quad (1)$$

where $w_1$, $w_2$, $w_3$ are normalized weighting factors that are inversely proportional to distances $d_1$, $d_2$, $d_3$ from 2D pixel $(x_p, y_p)$ to 2D vertices $(x_{s1}, y_{s1})$, $(x_{s2}, y_{s2})$, $(x_{s3}, y_{s3})$.

For example, if $d_1 = d_2 = d_3$, then $$w_1 = w_2 = w_3 = \frac{1}{3}.$$

As a second example, if $d_1 = d_2 = 2d_3$, then $$w_1 = w_2 = \frac{1}{4} \text{ and } w_3 = \frac{1}{2}.$$

In step 156 the processing unit determines the values of a respective triplet $[x_{wp}, y_{wp}, z_{wp}]$, according to equation (1), for each of the 2D pixels $(x_p, y_p)$ that fill 2D triangle 182.

In an association step 158, the values of each triplet $[x_{wp}, y_{wp}, z_{wp}]$, of the filled pixels in step 156, are associated with triangle 104A, forming a set {S} of triplets for the triangle, and the processing unit stores the set of triplets. It will be apparent from equation (1) that each triplet of set {S} is equivalent to a 3D point within triangle 104A.

In a decision step 160, the processing unit checks if a set of triplets, i.e., a set of 3D points within a given 3D triangle 104, has been stored for all 3D triangles in mesh 106. If a 3D triangle 104 exists without such a set, then the flowchart returns to step 152. If respective sets of 3D points have been stored for all triangles 104 in mesh 106, then the flowchart continues to a voxelization step 162.

In voxelization step 162 for each voxel of the 3D volume formed in step 151 PU 46 checks if at least one of the triplets stored in step 158 is contained in, or touches, the voxel. Such a voxel is "marked," or selected, as being assumed to be a voxel comprised in surface 22. All other voxels in the 3D volume, i.e., those not enclosing or touching a triplet stored in step 158, are assumed to be not comprised in surface 22.

PU 46 uses the voxel coordinates of the selected voxels to render image 70 of surface 22 on screen 74. It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for three-dimensional (3D) rendering, comprising:
   receiving a group of 3D triangles defining a triangular mesh of a surface, each 3D triangle in the group having three 3D vertices with respective 3D coordinates;
   transforming each 3D triangle into a corresponding two-dimensional (2D) triangle having three 2D vertices corresponding respectively to the 3D vertices, each 2D vertex having respective 2D pixel coordinates and a triplet of pixel attributes corresponding to the 3D coordinates of a corresponding 3D vertex;
   passing each 2D triangle to a graphics processor, which treats the triplet of pixel attributes of each 2D vertex as interpolatable values;
   in the graphics processor, computing respective triplets of interpolated pixel attributes for pixels within each 2D triangle by interpolation between the pixel attributes of the 2D vertices of the 2D triangle; and
   rendering a 3D image of the surface by converting the interpolated pixel attributes computed by the graphics processor into voxel coordinates in the 3D image.

2. The method according to claim 1, and comprising, after passing a given 2D triangle to the graphics processor, filling the given 2D triangle with the pixels within the given 2D triangle.

3. The method according to claim 1, wherein the interpolated pixel attributes comprise a weighted interpolation of the triplet of pixel attributes of each 2D vertex.

4. The method according to claim 3, wherein the weighted interpolation comprises applying a weight to the triplet of pixel attributes of a given 2D vertex that is inversely proportional to a distance of a given pixel to the given 2D vertex.

5. The method according to claim 1, wherein converting the interpolated pixel attributes into voxel coordinates comprises enclosing the triangular mesh in a rectangular parallelepiped of voxels, and selecting voxels containing or touching the interpolated pixel attributes as voxels of the surface.

6. The method according to claim 1, wherein the surface is comprised in a chamber of a heart.

7. The method according to claim 1, wherein each 2D triangle comprises one common 2D triangle.

8. The method according to claim 1, wherein each 2D triangle is configured to fill a virtual screen.

9. Apparatus for three-dimensional (3D) rendering, comprising:
   a processing unit configured to:
     receive a group of 3D triangles defining a triangular mesh of a surface, each 3D triangle in the group having three 3D vertices with respective 3D coordinates, and
     transform each 3D triangle into a corresponding two-dimensional (2D) triangle having three 2D vertices corresponding respectively to the 3D vertices, each 2D vertex having respective 2D pixel coordinates and a triplet of pixel attributes corresponding to the 3D coordinates of a corresponding 3D vertex; and
   a graphics processor configured to:
     receive each 2D triangle and to treat the triplet of pixel attributes of each 2D vertex as interpolatable values,
     compute respective triplets of interpolated pixel attributes for pixels within each 2D triangle by interpolation between the pixel attributes of the 2D vertices of the 2D triangle, and
   wherein the processing unit is configured to render a 3D image of the surface by converting the interpolated pixel attributes computed by the graphics processor into voxel coordinates in the 3D image.

10. The apparatus according to claim 9, wherein the graphics processor is configured to fill a given 2D triangle with the pixels.

11. The apparatus according to claim 9, wherein the interpolated pixel attributes comprise a weighted interpolation of the triplet of pixel attributes of each 2D vertex.

12. The apparatus according to claim 11, wherein the weighted interpolation comprises applying a weight to the triplet of pixel attributes of a given 2D vertex that is inversely proportional to a distance of a given pixel to the given 2D vertex.

13. The apparatus according to claim 9, wherein the processing unit is configured to enclose the triangular mesh in a rectangular parallelepiped of voxels, and to select voxels containing or touching the interpolated pixel attributes as voxels of the surface.

14. The apparatus according to claim 9, wherein the surface is comprised in a chamber of a heart.

15. The apparatus according to claim 9, wherein each 2D triangle comprises one common 2D triangle.

16. The apparatus according to claim 9, wherein each 2D triangle is configured to fill a virtual screen.

* * * * *